(12) United States Patent
Grader et al.

(10) Patent No.: US 10,247,852 B2
(45) Date of Patent: Apr. 2, 2019

(54) CONDITIONING OF EXPANDED POROSITY

(71) Applicant: INGRAIN, INC., Houston, TX (US)

(72) Inventors: Abraham S. Grader, Houston, TX (US); Jonas Toelke, Houston, TX (US); Yaoming Mu, Houston, TX (US); Michael Suhrer, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 340 days.

(21) Appl. No.: 14/909,957

(22) PCT Filed: Aug. 8, 2014

(86) PCT No.: PCT/US2014/050412
§ 371 (c)(1),
(2) Date: Feb. 3, 2016

(87) PCT Pub. No.: WO2015/021424
PCT Pub. Date: Feb. 12, 2015

(65) Prior Publication Data
US 2016/0170088 A1    Jun. 16, 2016

Related U.S. Application Data (60) Provisional application No. 61/863,508, filed on Aug. 8, 2013.

(51) Int. Cl.
*G06F 17/50* (2006.01)
*G01V 99/00* (2009.01)
(Continued)

(52) U.S. Cl.
CPC ........... *G01V 99/005* (2013.01); *G01N 33/24* (2013.01); *G06F 17/5009* (2013.01); *G01N 23/046* (2013.01)

(58) Field of Classification Search
USPC ................. 703/2, 10, 22; 345/581; 702/6
See application file for complete search history.

(56) References Cited

U.S. PATENT DOCUMENTS 4,783,751 A * 11/1988 Ehrlich ............... G01N 15/088
                                                         345/581
7,277,795 B2 * 10/2007 Boitnott ............... G01V 11/00
                                                         702/6

(Continued)

FOREIGN PATENT DOCUMENTS

| EP | 2124042 | 11/2009 |
|---|---|---|
| WO | 2012/118866 | 9/2012 |
| WO | 2015/021424 | 2/2015 |

OTHER PUBLICATIONS

"Extended EP Search Report", dated Feb. 17, 2017, Appl No. 14835085.3, "Conditioning of Expanded Porosity," Filed Aug. 8, 2014, 10 pgs.

"PCT Search Report and Written Opinion", dated Nov. 18, 2014, Appl No. PCT/US2014/050412, "Conditioning of Expanded Porosity," Filed Aug. 8, 2014, 14 pgs.

(Continued)

*Primary Examiner* — Thai Q Phan
(74) *Attorney, Agent, or Firm* — Chamberlain Hrdlicka (57) ABSTRACT

Methods and systems for conditioning expanded porosity, including a method that includes creating a disconnected pore structure by reducing the pore sizes of a rock sample's scanned image, identifying expanded pores within the rock sample and generating an expanded pore image from the expanded pores. The method further includes combining the expanded pore image with the scanned image to create an expansion mask, generating a grain conditioning volume based on at least one unexpanded region of the rock sample, combining the grain conditioning volume with the expansion mask to generate a fill volume image, combining the fill volume image with the scanned image to create an unex- (Continued)

panded volume image, and generating and presenting to a user a formation log using a model generated based upon the unexpanded volume image.

26 Claims, 7 Drawing Sheets (51) Int. Cl.
  *G01N 33/24* (2006.01)
  *G01N 23/046* (2018.01)

(56) References Cited

U.S. PATENT DOCUMENTS

| | | | | |
|---|---|---|---|---|
| 8,311,788 | B2* | 11/2012 | Hurley | G06T 17/00 |
| | | | | 703/10 |
| 8,725,477 | B2* | 5/2014 | Zhang | E21B 49/00 |
| | | | | 703/10 |
| 9,121,808 | B2* | 9/2015 | Leyte Guerrero | G01N 15/088 |
| 9,581,723 | B2* | 2/2017 | Hurley | G01V 11/00 |
| 2009/0259446 | A1 | 10/2009 | Zhang et al. | |
| 2010/0135536 | A1 | 6/2010 | Dvorkin et al. | |
| 2012/0281883 | A1 | 11/2012 | Hurley et al. | |
| 2015/0355158 | A1* | 12/2015 | Lander | G01N 33/24 |
| | | | | 702/2 |

OTHER PUBLICATIONS

Adalsteinsson, David et al., "Accurate and Efficient Implementation of Pore-Morphology-based Drainage Modeling in Two-dimensional Porous Media", Transport in Porous Media (2006) 65: 337-358, © Springer 2006, DOI 10.1007/s11242-005-6091-6, 22 pgs.
Hazlett, R. D., "Simulation of Capillary-Dominated Displacements in Microtomographic Images of Reservoir Rocks", Transport in Porous Media 20:21-35, 1995, 'KluwerAcademic Publishers. Printed in the Netherlands., 15 pgs.
Hilpert, Markus et al., "Pore-Morphology-Based Simulation of Drainage in Totally Wetting Porous Media", Advances in Water Resources 24 (2001), p. 243-255, Elsvier Science Ltd., 13 pgs.
PCT International Search Report and Written Opinion, dated Nov. 18, 2014, Appl No. PCT/US2014/050412, "Conditioning of Expanded Porosity," Filed Aug. 8, 2014, 14 pgs.
Adalsteinsson, David, et al., "Accurate and Efficient Implementation of Pore-Morphology-based Drainage Modeling in Two-dimensional Porous Media," Transport in Porous Media (2006) 65: 337-358, © Springer 2006, DOI 10.1007/s11242-005-6091-6.
Hazlett, R. D., "Simulation of Capillary-Dominated Displacements in Microtomographic Images of Reservoir Rocks," Transport in Porous Media 20:21-35, 1995, 'KluwerAcademic Publishers. Printed in the Netherlands.
Hilpert, Markus, et al., "Pore-Morphology-Based Simulation of Drainage in Totally Wetting Porous Media," Advances in Water Resources 24 (2001), p. 243-255, Elsvier Science Ltd.

* cited by examiner

CONDITIONING OF EXPANDED POROSITY

CROSS-REFERENCE TO RELATED APPLICATION

This application claims priority to Provisional U.S. Application Ser. No. 61/863,508, titled "Conditioning of Expanded Porosity" and filed Aug. 8, 2013 by Abraham Grader, Jonas Toelke, Yaoming Mu and Michael Shurer [sic: Suhrer], which is incorporated herein by reference.

BACKGROUND

X-ray computed microtomography offers scientists and engineers a way to gain a better understanding of the materials with which they work. Under high magnification, it becomes evident that many materials (including rock and bone) have a porous microstructure that permits fluid flows. Such fluid flows are often of great interest, e.g., in subterranean hydrocarbon reservoirs. Accordingly, significant efforts have been expended to characterize materials in terms of their flow-related properties including porosity, permeability, and the relation between the two.

Scientists typically characterize materials in the laboratory by applying selected fluids with a range of pressure differentials across the sample. Such tests often require weeks and are fraught with difficulties, including requirements for high temperatures, pressures, and fluid volumes, risks of leakage and equipment failure, and imprecise initial conditions. Flow-related measurements are generally dependent not only on the applied fluids and pressures, but also on the history of the sample. Any tests preferably should begin with the sample in a native state, but this state is difficult to achieve once the sample has been removed from its original environment. Some rock cores (e.g., oil-bearing unconsolidated sands) deform as they are retrieved from the surface from the high-pressure downhole environment. Much of this deformation is attributable to gases evolving out of solution, expanding and escaping from the core sample. This expansion creates zones of high porosity as grains move around to create escape paths for the gas. The deformation results in an over-estimation of porosity and permeability values, thus making it difficult to determine the original petrophysical properties for the formation, both static (e.g., porosity, permeability and formation factor) and dynamic (e.g., relative permeability, capillary pressure and Archie's saturation exponent). Conventional laboratory methods do not address this issue as physical recompaction techniques used in such methods do not return the sample to its original condition.

BRIEF DESCRIPTION OF THE DRAWINGS

A better understanding of the various disclosed embodiments can be obtained when the following detailed description is considered in conjunction with the attached drawings, in which.

It should be understood that the drawings and corresponding detailed description do not limit the disclosure, but on the contrary, they provide the foundation for understanding all modifications, equivalents, and alternatives falling within the scope of the appended claims.

DETAILED DESCRIPTION

The paragraphs that follow describe illustrative methods and systems for performing conditioning of expanded porosity. Illustrative drilling environments are first described, followed by a description of high resolution scanning and imaging of rock fragments obtained as cuttings or core samples obtained during the drilling process. The resulting digital representations of the rock produced are processed to identify regions where the rock has expanded, and additional processing estimates the pore size of the rock in its original pressurized downhole environment. Once the pore size is adjusted, rock properties such as, for example, permeability are estimated, enabling the production of one or more logs estimating the properties of the rock as a function of depth. The disclosed methods are also presented within the context of an illustrative system and a software-based implementation by said system. Together, the system and software may perform at least part of the disclosed methods to characterize the formation and produce an estimated log of its properties.

Figure 1:
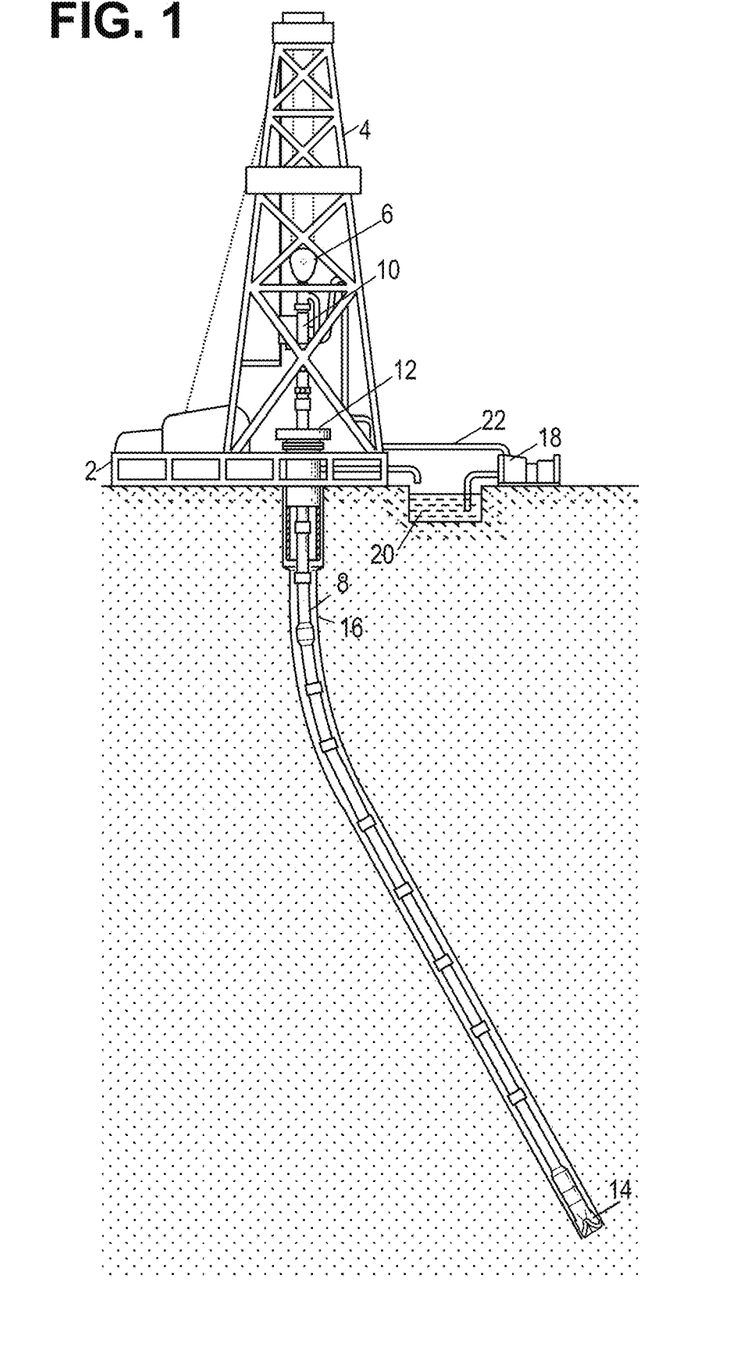
FIG. 1 is a schematic diagram of an illustrative drilling environment.

The disclosed methods and systems are best understood in the context of the larger systems in which they operate. Accordingly, FIG. 1 shows an illustrative drilling environment. A drilling platform 2 supports a derrick 4 having a traveling block 6 for raising and lowering a drill string 8. A top drive 10 supports and rotates the drill string 8 as it is lowered through the wellhead 12. A drill bit 14 is driven by a downhole motor and/or rotation of the drill string 8. As bit 14 rotates, it creates a wellbore 16 that passes through various formation layers. A pump 18 circulates drilling fluid 20 through a feed pipe 22, through the interior of the drill string 8 to drill bit 14. The fluid exits through orifices in the drill bit 14 and flows upward through the annulus around the drill string 8 to transport cuttings to the surface. At the surface, the drilling fluid is filtered to remove the cuttings and the drilling fluid is recirculated back down the drill string 8 to repeat the process.

The cuttings filtered out from the drilling fluid are representative of the rock formation depth interval from which they originate from. These cuttings may be analyzed using the disclosed systems and methods. Alternatively, core samples may be used such as, for example, sidewall cores and whole cores, as well as outcrop quarrying samples. Other sample sources suitable for use with the disclosed systems and methods will become apparent to those of ordinary skill in the art, and all such sample sources are within the scope of the present disclosure.

Figure 2:
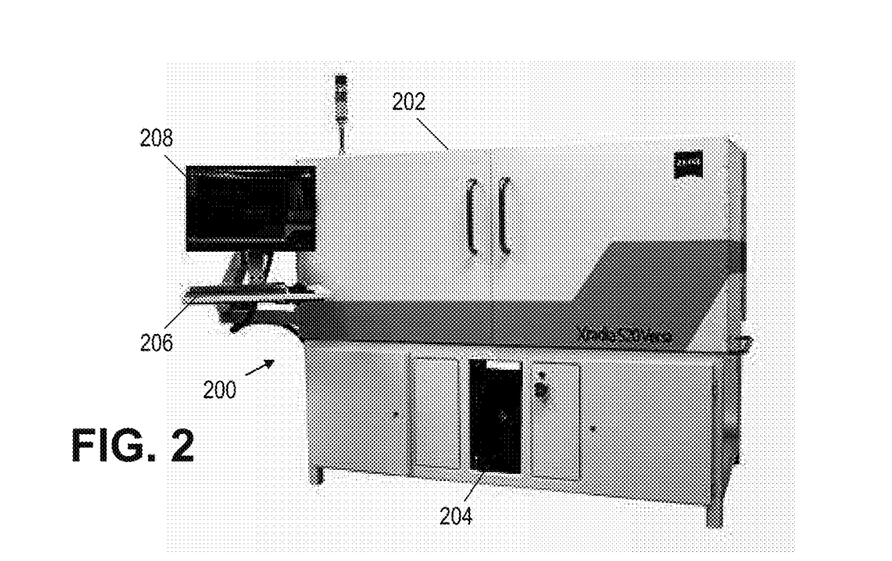
FIG. 2 is an image of an illustrative high resolution X-ray microtomography scanner.

Once obtained, the rock samples are scanned using any of a number of scanning technologies. In at least some illustrative embodiments, a high-resolution X-ray microtomography scanner such as that shown in FIG. 2 is used to scan the sample. Scanner 200 has an observation chamber 202 in which the sample is placed, which is coupled to a computer 204 that controls the measurement of the sample. Software on the computer 204 interacts with a user via a user interface having one or more input devices 206 (e.g., a keyboard, mouse, joystick, light pen, touchpad and/or touchscreen) and one or more output devices 208 (e.g., a display and/or a printer).

In the illustrative example, high resolution imaging is achieved by scanning the sample from multiple angles with a beam of X-rays and the measured intensity of the signals is subjected to a tomographic reconstruction process to obtain two-dimensional slices that are combined to produce three-dimensional volumes. Throughout the present disclosure the term "image" is used to describe both two-dimensional and three dimensional images representing the rock samples. Further, although at least some illustrative embodiments utilize X-ray microtomography to image the sample, other technologies are also suitable to produce images of the rock usable by the disclosed systems and methods to produce a digital model of the sample. These technologies include, but are not limited to, scanning acoustic microscopy (SAM), magnetic resonance imaging (MRI), transmitted laser scanning confocal microscopy (LSCM) and focused ion beam scanning electron microscopy (FIB-SEM). Other suitable technologies that provide sufficient resolution to image the porosity structure of the sample will become apparent to those of ordinary skill in the art, and all such technologies are within the scope of the present disclosure.

Figure 3:
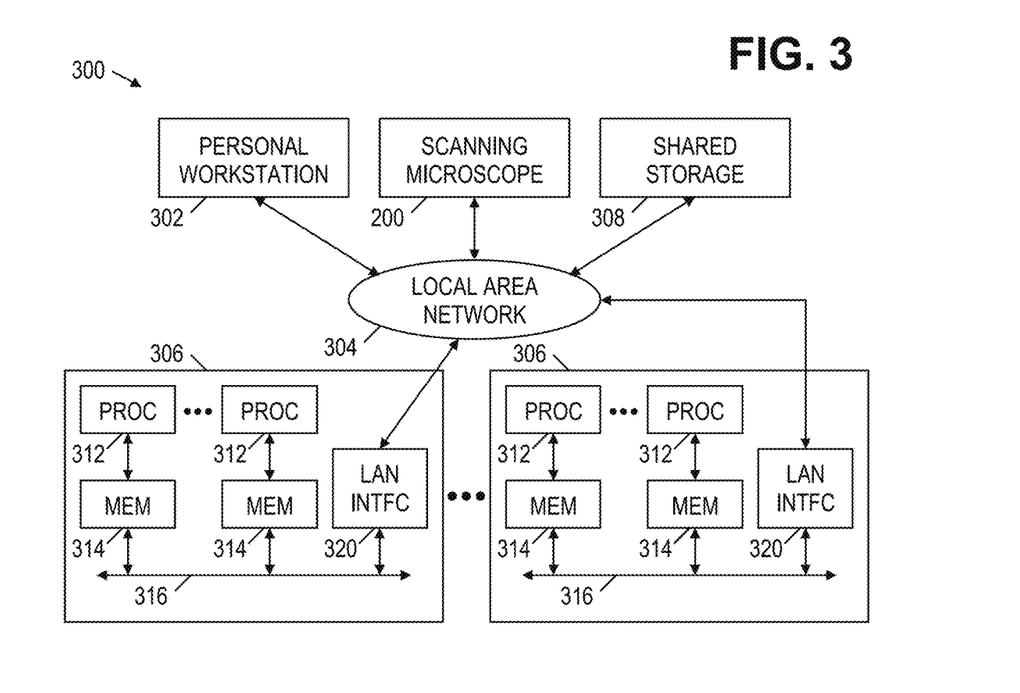
FIG. 3 is an image of an illustrative high performance computing network.

In at least some illustrative embodiments, Scanner 200 of FIG. 2 may be part of an analysis system such as system 300 of FIG. 3. System 300 includes a personal workstation 302 that is coupled to scanner 200 by local area network (LAN) 304. LAN 304 further enables intercommunication between scanner 200, personal workstation 302, one or more high performance computers 306 and one or more shared storage devices 308 (e.g., RAID, NAS and/or SAN devices). In at least some illustrative embodiments, computers 306 operate as servers within a client/server configuration. Each computer 306 may include multiple processors 312 coupled to each other, local memory 314 and a network interface 320 by internal bus 316. In at least some illustrative embodiments, parallel processing software resident in memories 314 enable the processors 312 to cooperatively identify, distribute and execute tasks to be performed in parallel, each processor communicating with shared storage device 308 as needed to store results and to access input data and/or intermediate results.

In the illustrative embodiment of FIG. 3, a user employs personal workstation 302 (e.g., a desktop or laptop computer) to interact with system 300. Software executing on the processors 302 provides a user interface the enables the user, for example, to control the scanning of the samples and the production of images, to view the resulting images and to control the generation and use of rock models based upon the images. Tasks that have relatively small computational demands may be performed on personal workstation 302, while computationally demanding tasks may be performed by one or more of the computers 306. In at least some illustrative embodiments, personal workstation 302 operates as client within a client/server configuration.

Figure 4A:
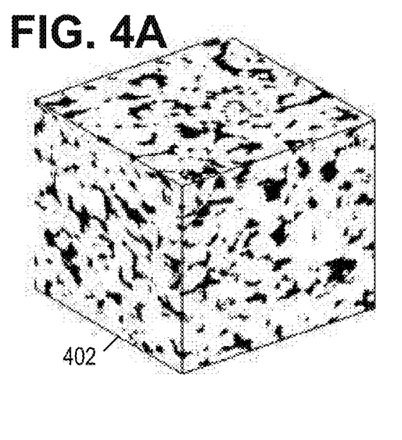
FIG. 4A is an image of an illustrative volumetric representation of a sample.
Figure 4B:
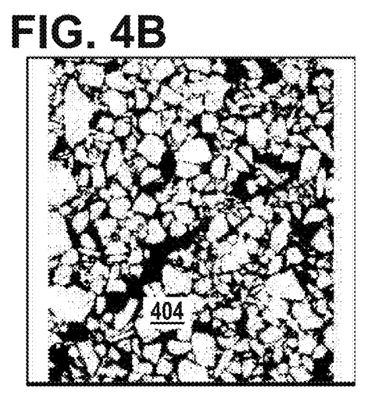
FIG. 4B is an image of an illustrative cross-section of a sample

FIG. 4A shows an illustrative scanned image 402 of a rock sample, produced by a scanner such as scanner 200. The image is composed of three-dimensional volume elements referred to as "voxels," each associated with a value indicative of the composition of the sample at the corresponding location within the sample volume. When the image is processed, each voxel is categorized as representing either a pore or a portion of the rock matrix. The result is a pore/matrix model wherein each voxel is represented by a single bit that indicates whether the model at the volume location of the voxel is either pore space or matrix material. Such a pore/matrix model is a useful starting point for a variety of analyses, including but not limited to porosity and permeability measurements. FIG. 4B shows an illustrative image wherein pore space is shown in black and matrix material is depicted as white space.

As previously noted, at least some samples may suffer deformation from gas expansion, as well as other mechanical effects, when brought to the surface. Such samples may exhibit expansion regions having substantially enlarged pores, such as the elongated pore 404 in FIG. 4B. The disclosed systems and methods operate to identify such expanded regions and "fill in" at least some of the enlarged pores with grain structures from unexpanded portions of the sample, thus obtaining, a digital rock image representative of the expanded formation. The modified image may subsequently be used as a basis for determining representative static and dynamic formation properties, as previously described.

Figure 5:
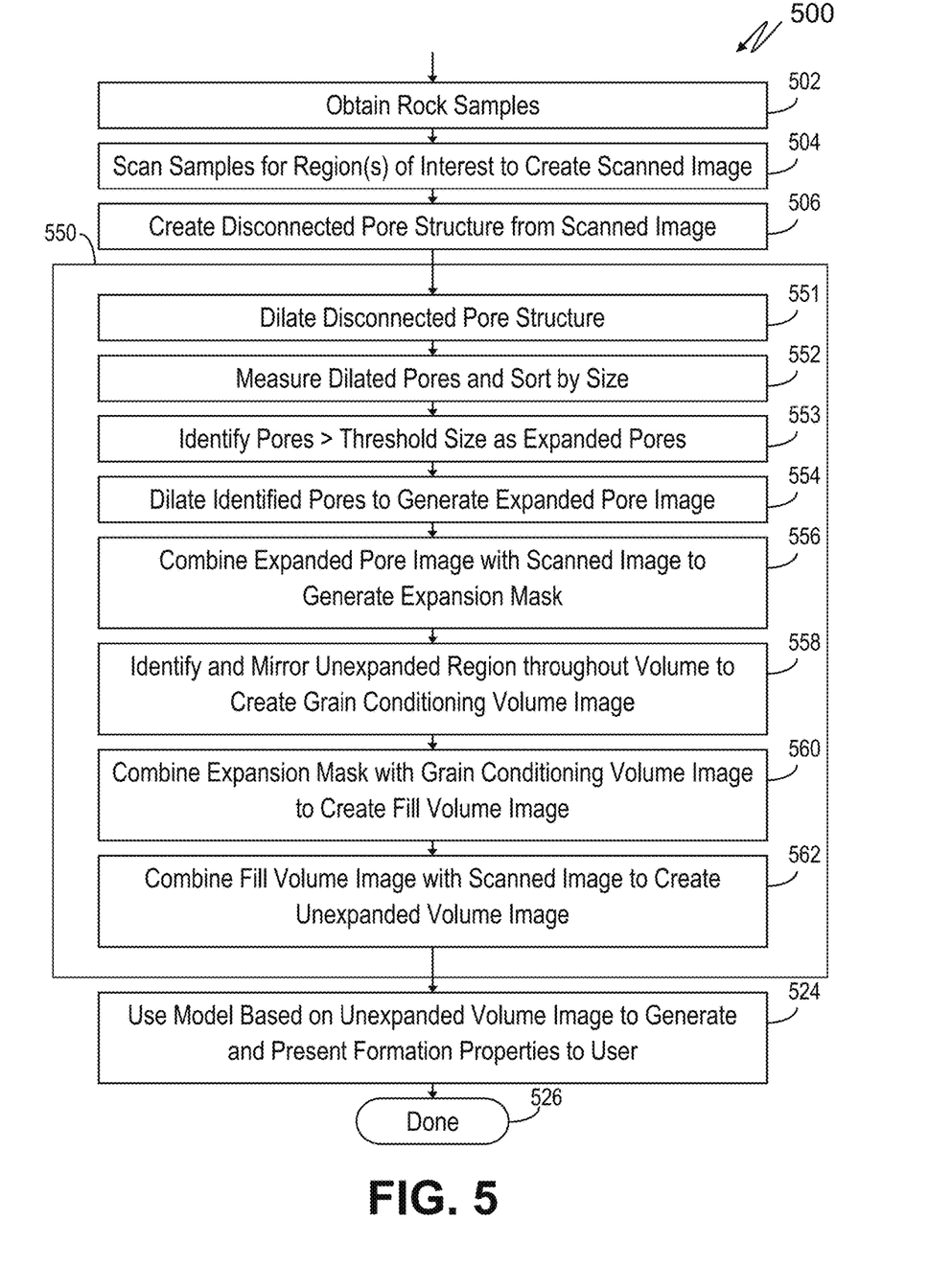
FIG. 5 is a flowchart showing an illustrative method for conditioning expanded porosity.
Figure 6:
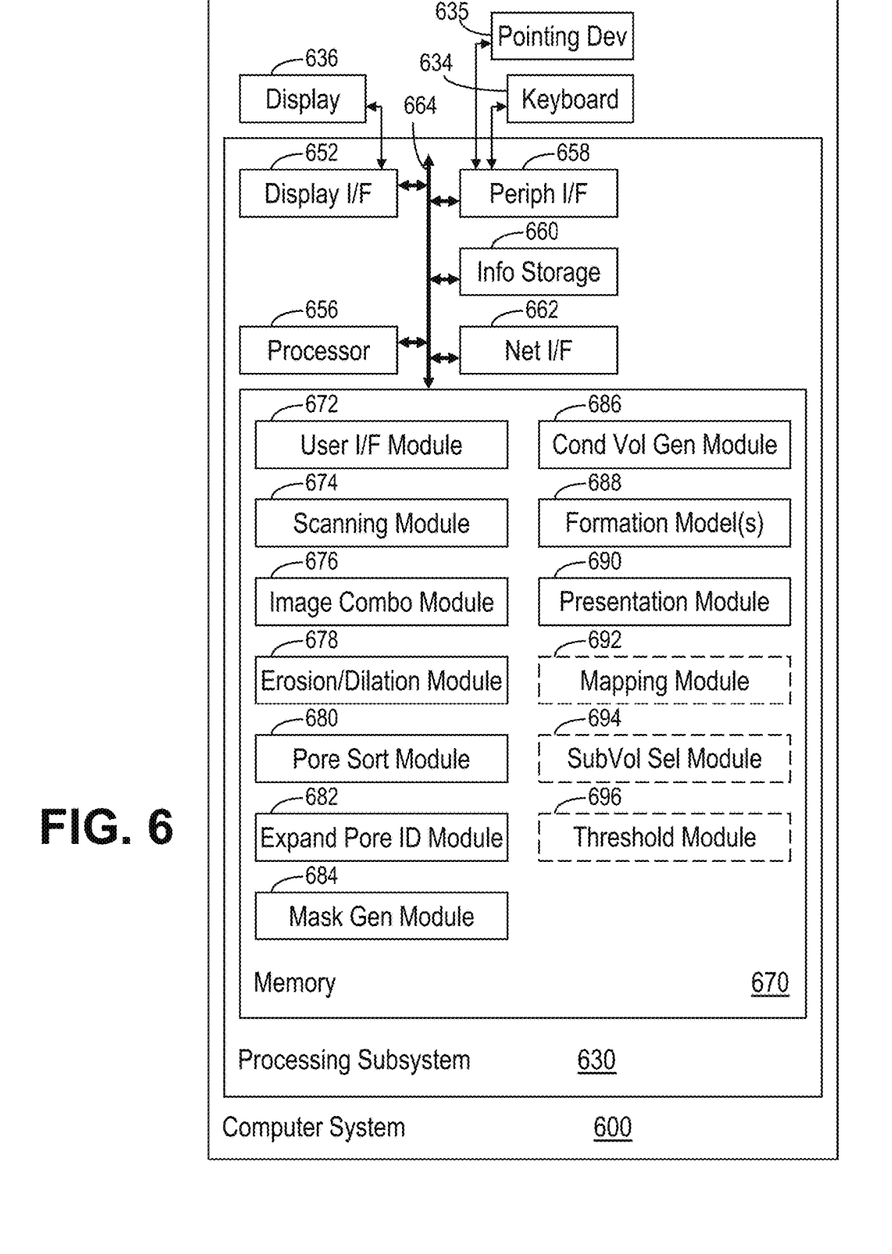
FIG. 6 is a block diagram of a computer system suitable for implementing at least part of the disclosed methods in software.

FIG. 5 shows an illustrative flowchart for such a method, while FIG. 6 shows a block diagram of a computer system 600. Both hardware and software components of computer system 600 are shown, which in at least some illustrative embodiments implement at least part of the conditioning of expanded porosity shown as method 500 in FIG. 5 (described in detail below). A user may interact with computer system 600 via keyboard 634, pointing device 635 (e.g., a mouse) and display 636 to configure, control and monitor the execution of the conditioning of expanded porosity. Although shown and described for simplicity as a single computer system 600, the same functionality may also be implemented by a distributed system such as system 300 of FIG. 3.

Located within processing subsystem 630 of computer system 600 is a display interface 652, a processor 656, a peripheral interface 658, an information storage device 660, a network interface 662 and a memory 670. Bus 664 couples each of these elements to each other and transports their communications. Network interface 662 enables communications with other systems (e.g., via the Internet with a central database server housing well logging data). In accordance with user input received via peripheral interface 658 and program instructions from memory 670 and/or information storage device 660, processor 656 processes input from the user and applies it to the well logging data to perform the disclosed methods and present the results to the user. Storage device 660 may be implemented using any number of known non-transitory information storage media, including but not limited to magnetic disks, solid-state storage devices and optical storage disks.

Various software modules are shown loaded into memory 670 of FIG. 5, where they are each accessed by processor 656 for execution. These modules include: User Interface Module 672, which interacts with the input/output devices utilized by the user to interact with processing system 630; Scanning Module 674, which controls the scanning of a rock sample and/or performs the initial processing of scan data; Image Combination Module 676, which combines volume images to generate other volume images; Erosion/Dilation Module 678, which performs erosion and/or dilation of the volume image pores; Pore Sort Mask 680, which sorts the pores by size; Expanded Pore ID Module 682, which identifies the expanded pores of the rock sample; Mask Generation Module 684 which generates the expansion mask; Grain Conditioning Volume Generation Module 686, which generates the grain conditioning volume image; Formation Model(s) 688, which models the formation based upon one or more volume images; Presentation Module 690, which generates and presents formation properties to the user; optional Mapping Module 692, which generates open maps; optional Subvolume Selection Module 694, which selects subvolumes based on the absence of expanded pores space; and optional threshold module 696, which dynamically adjusts the pore size threshold used to identify expanded pores. In at least some illustrative embodiments, the results are presented by Presentation Module 690 in graphical form (e.g., as an image of the various bed layers of a formation within a wellbore depth range), while in other illustrative embodiments the results are presented as well logs.

Referring now to both FIGS. 5 and 6, illustrative method 500 begins by obtaining rock samples from one or more depth intervals of interest (block 502). The samples are cleaned if necessary, and scanned using any of the previously described techniques to produce an initial scanned image of the sample (block 504; Scanning Module 674). The selected scanning technique preferably provides a resolution that is sufficiently high to distinguish between the rock's matrix and its pores, thus permitting construction of the pore/matrix model as described herein. The scanned image is segmented into solids and pores to create a three-dimensional pore structure, which may include expanded regions with large pores that did not exist in the rock sample before it was brought to the surface.

The resulting pore structure is subjected to an erosion procedure, wherein the pores are shrunk until large pores separate from other pores, causing the pores to become disconnected (block 506; Erosion/Dilation Module 678). An example of such an erosion procedure is described in M. Hilpert, C. T. Miller, *Pore-morphology-based simulation of drainage in totally wetting porous media*, Adv. Water Resour. 24, 243 (2001). The pores may be classified as "large" using several techniques such as, e.g., estimating the pores' dimensions and comparing the sizes to other pores (i.e., the pore size distribution). "Large" pores are those that, after being dilated, exceed a threshold value. Such a value may be preprogrammed or set interactively by a user based on the pore size distribution.

The above-described erosion results in the elimination of small pores within unexpanded regions of the scanned image. As the erosion procedure is repeated, the number of iterations required to reach the disconnected state is recorded. Once the disconnected state is reached, a dilation procedure is applied that re-expands the eroded pores to produce a disconnected pore structure (block 551; Erosion/Dilation Module 678). It should be noted that this dilation is not a true inversion of the erosion procedure, as the small pores eliminated by the erosion do not reappear when the dilation is performed. Further, after performing dilation for the recorded number of iterations, the large pores will typically remain disconnected.

Figure 7A:
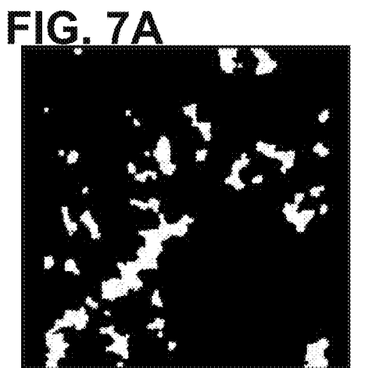
FIGS. 7A-7C illustrate examples of intermediate results of at least some of the illustrative methods described.

In at least some illustrative embodiments, once the dilation is performed, the resulting disconnected pores of the disconnected pore structure are measured and sorted by size (block 552; Pore Sort module 680). A threshold value is used to divide the pores into two groups: expanded pores and unexpanded pores. This threshold value may be a fixed preprogrammed value (e.g., a general rule of thumb), or a variable value set by a user operating computer system 600 interactively. Pores of sizes larger than the cutoff threshold size are identified as expanded pores while pores at or below the threshold size are identified as unexpanded pores (block 553; Expanded Pore ID Module 682). FIG. 7A shows an image resulting from applying the threshold size in this manner to the image of FIG. 4B, wherein the pore space is shown in white.

Figure 7B:
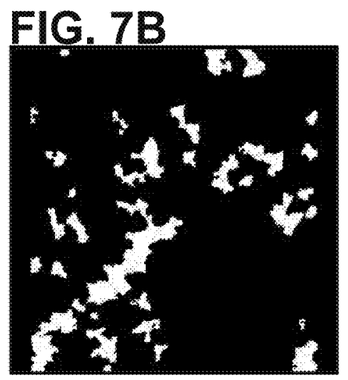

The resulting image is further dilated (e.g., by one additional pixel) to generate the expanded pore image (block 554; Erosion/Dilation Module 678). The expanded pore image is combined with the original scanned image to generate an expansion mask (block 556; Mask Generation Module 684). This mask operates to identify those portions of the original pore structure that are attributable to expansion (the "expanded pore space" or "expanded pore volume"). FIG. 7B shows an illustrative expansion mask, wherein the expanded pore space is shown in white.

Once the expanded pore space has been identified, a representative sub-region of an unexpanded region of the rock sample is identified so it can be used to replace the identified expanded pore space of the three-dimensional rock sample image. In at least some illustrative embodiments, a subvolume is defined within the volume of the original scanned three-dimensional image of the rock sample. The subvolume selected is one that has the least number of expanded pores, thus representing an unexpanded region of the rock sample. This selection may be automated or alternatively may be based on an interactive session with a user. It should be noted that there may be a variety of nearly equivalent subvolumes from which the system or a user can select an appropriate subvolume, i.e., a subvolume that appears characteristic of the rock sample. Preferably, the largest subvolume that can be defined within the rock sample volume that has no expanded pores is selected. If no such subvolume can be defined that is above a minimum subvolume size, the subvolume above the minimum subvolume size that has the least number of expanded pores is selected. The minimum subvolume size may be preprogrammed, or set interactively by a user and depends at least in part on the pore structure of the rock sample. Such a minimum size threshold avoids using subvolumes that would produce a mirrored image that is too repetitive and thus not representative of the rock sample as a whole. Once the subvolume is identified, it is mirrored throughout the volume of the scanned image to create a grain conditioning volume image that is the same size as the original rock sample image or "digital rock" (block 558; Grain Conditioning Volume Generation Module 686).

Figure 7C:
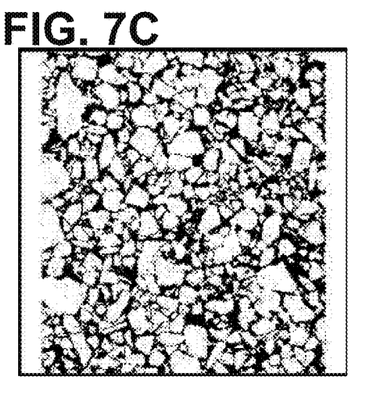

In at least some illustrative embodiments, the grain conditioning volume image is combined with the expansion mask to create a fill volume image (block 560; Image Combination Module 676). This image is a replacement mask that provides representative unexpanded pores from the grain conditioning volume in the shape of the voids created by the expanded pore volume. This fill volume image is combined with the original scanned image to create an unexpanded volume image (block 562; Image Combination Module 676), thus creating an unexpanded rock model. FIG. 7C shows an illustrative result of the creation of the unexpanded volume image, wherein the pores space is shown in black. A comparison with FIG. 4B reveals that the expanded pore space has been largely eliminated. A formation model based on the pore characteristics of the unexpanded volume image is used to generate and present to a user static and dynamic formation properties that reflect the behavior of the unexpanded rock at its original depth (block 524; Formation Model(s) 688 and Presentation Module 690), ending the method 500 (block 526). In at least some illustrative embodiments, the results produced by the model are presented as formation logs such as those shown in FIG. 8.

Figure 5A:
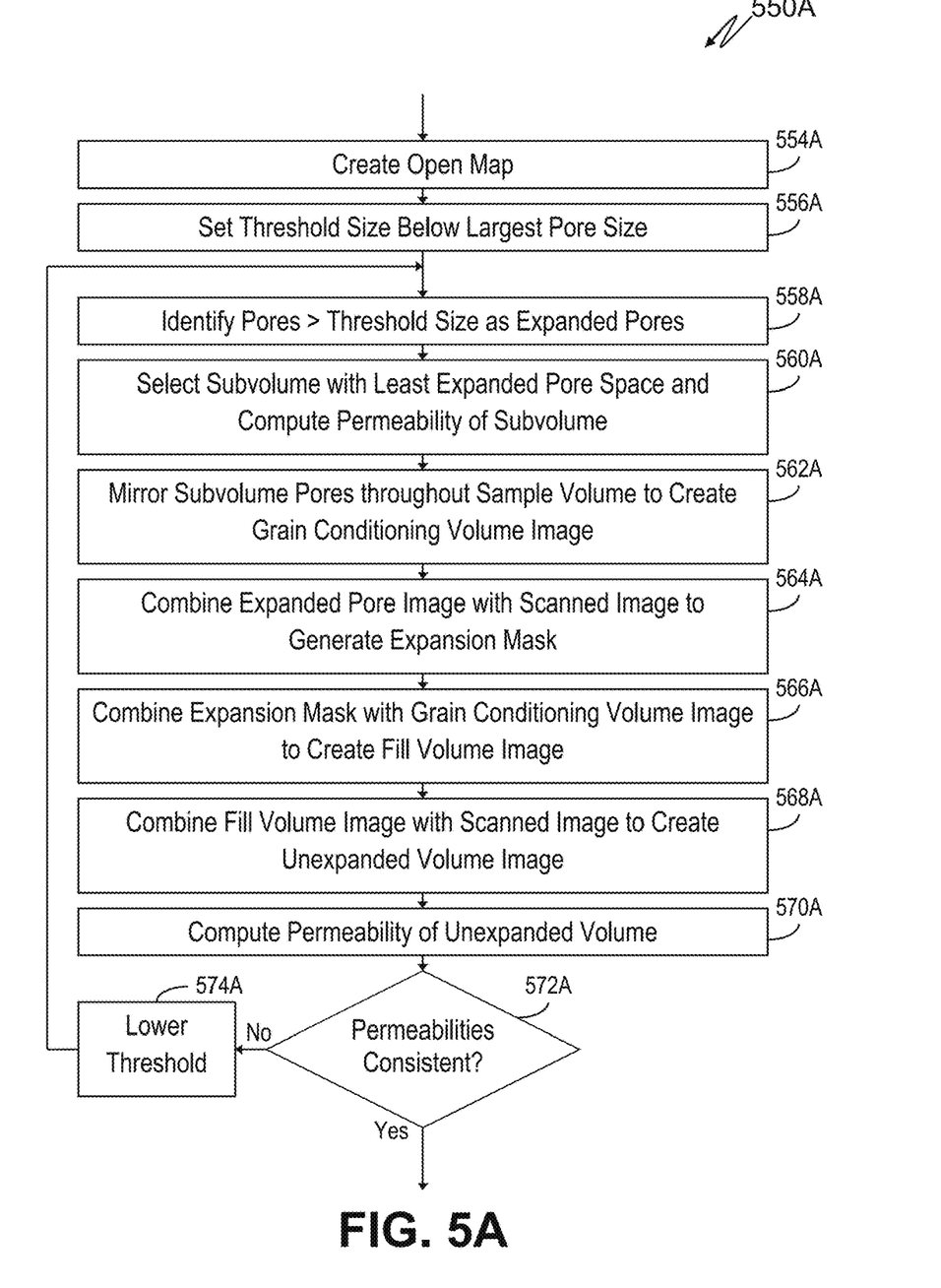
FIG. 5A is a flowchart of an alternative illustrative implementation of part of the method of FIG. 5.
Figure 8:
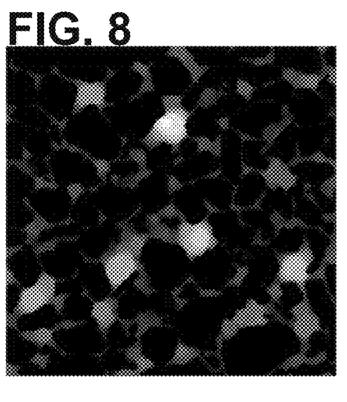
FIG. 8 shows an example of an illustrative open map.

FIG. 5A illustrates an alternative embodiment for the blocks within grouping block 550 of FIG. 5 (blocks 551-562), which provides an alternative sub-method 550A for identifying the expanded pores of the rock sample and substituting them with representative unexpanded regions of the same rock sample. Referring to both FIGS. 5 and 5A, once the disconnected pore structure has been created (block 506), the identification of the expanded pores begins with the creation of an open map (block 554A; Mapping Module 692). Within such an open map, each pore voxel is assigned a value representative of the radius of the largest sphere that can be inscribed within the pore space without intersecting a solid matrix voxel. The value thus describes the openness of the pore space, with smaller values indicating that the voxel is part of a smaller feature or pore space of the rock sample, and larger values indicating that the voxel is part of a larger feature or pore space. This may be represented as shown in FIG. 8, where darker greyscale values represent smaller features, and lighter greyscale values represent larger features. Solid matrix grains are shown in black. Once the open map is created, the threshold size value is then set (e.g., interactively by a user) to just below the largest pore size (block 556A; Threshold Module 696). Pores of sizes larger than the cutoff threshold size are identified as expanded pores while pores at or below the threshold size are identified as unexpanded pores (block 558A; Expanded Pore ID Module 682).

Separating the voxels at a certain threshold pore radius $r_t$ of the open map operates as an approximation of the wetting and non-wetting phase at the capillary pressure $2\sigma/r_t$. A graph of the cumulative values of the pore volume occupied by the values larger than the threshold value provides a cumulative pore size distribution. This pore size distribution is strongly related to the hydraulic radius of a give pore shape (herein referred to as a hydraulic pore size distribution) and is useful for predicting fluid flow transport properties. The combination of all the identified expanded pores represents the expanded pore volume of the rock sample.

It should be noted that the value assigned to each voxel (i.e., the size of the pore associated with the voxel) may be determined using other techniques. In at least some illustrative embodiments, a pore-size distribution providing the values assigned to each voxel is derived from a direct segmentation of the three-dimensional pore space of the rock sample. The pore space is segmented by applying three-dimensional morphological and quantitative image operations to a computed distance map of the target pore space. The pore sizes of the of the segmented pores are computed by the ratio of the volume to the surface of the individual pores, producing frequency and cumulative distributions for pore populations and volumes, with the results being produced at particular nuclear magnetic resonance (NMR) effective diameters (the pore size distribution of this embodiment herein referred to as a digital NMR pore size distribution). Other techniques for determining the pore space sizes will become apparent to those of ordinary skill in the art, and all such techniques are within the scope of the present disclosure.

Once the expanded pore volume is identified, an unexpanded region is defined as a subvolume with the rock sample's volume and the permeability of the subvolume is computed using a formation model (block 560A; SubVolume Selection Module 694 and Formation Model(s) 688). The subvolume defined and selected based on having the least number of expanded pores (as described above), thus representing an unexpanded region of the rock sample. The subvolume is then mirrored throughout the sample rock's volume to create the grain conditioning volume image (block 562A; Grain Conditioning Volume Generation Module 686). The expanded pore image is combined with the original scanned image to generate an expansion mask (block 564A; Mask Generation Module 684), and the grain conditioning volume image is combined with the expansion mask to create a fill volume image (block 566A; Image Combination Module 676) The volume image in turn is combined with the original scanned image to create the unexpanded volume image (block 568A; Image Combination Module 676), and the permeability of the unexpanded volume image is computed using a formation model (block 570A; Formation Model(s) 688).

In at least some illustrative embodiments, the permeability values for the subvolume and the unexpanded volume are compared and the difference between them is used to determine the degree of consistency between the subvolume and the unexpanded volume. If the difference is at or below a tolerance value (block 572A; Threshold Module 596), the permeabilities are consistent and the formation model is used to generate and present to a user static and dynamic formation properties that reflect the behavior of the unexpanded rock at its original depth (block 524; Formation Model(s) 688 and Presentation Module 690), ending the method 500 (block 526). If the difference between computed permeabilities is above the tolerance value, the permeabilities are inconsistent and the threshold is lowered (blocks 572A and 574A; Threshold Module 596). Once the threshold is adjusted, blocks 558A-574A are repeated as needed until the permeabilities are consistent, or a non-convergence limit is reached (e.g., a maximum number of iterations). In at least some illustrative embodiments, if the permeabilities fail to converge the method may be aborted. In other illustrative embodiments, sub-method 550A may be repeated using one or more alternative techniques for defining the grain conditioning volume image if the permeabilities fail to converge.

One example of an alternative technique for creating a grain conditioning volume image from a mirroring-extended subvolume (suitable, for example, when a sample region sufficiently lacking expanded pores space cannot be identified) is employing an offset or "shifted" version of the original scanned volume image. In at least some illustrative embodiments the shift is performed in a circular manner, with those portions of the volume image that are shifted outside a volume boundary being shifted back into the volume image across the opposite boundary, as if the scanned volume image where a representative unit of a periodic structure. In alternative embodiments, the entire scanned image volume is mirrored to create an extended model, and the above-described shift is performed on the extended model to create the grain conditioning volume image.

Another alternative embodiment creates the grain conditioning volume image by "slicing and shuffling the original scanned image volume by dividing the volume into multiple subvolumes and rearranging the subvolume, either systematically or randomly. In at least some illustrative embodiments a rotational and/or mirroring transformation is additionally or alternatively applied to the original scanned image volume as a whole. In other illustrative embodiments, such a rotational/mirroring transformation is applied to the individual subvolumes, either systematically or randomly.

In yet another illustrative embodiment, suitable for example where the original scanned volume image has an unusually heterogeneous distribution of grain sizes, the creation of the grain conditioning volume image is performed using any of the above-described methods and systems on a modified scanned image volume. The modified volume omits those larger grains that are unlikely to have shifted as part of the expansion (i.e., large grains are treated as expanded pore space). By omitting the larger grains from the creation of the grain conditioning volume, the resulting volume has a larger number of smaller unexpanded grains and is thus more representative of the unexpanded rock sample.

Figure 9:
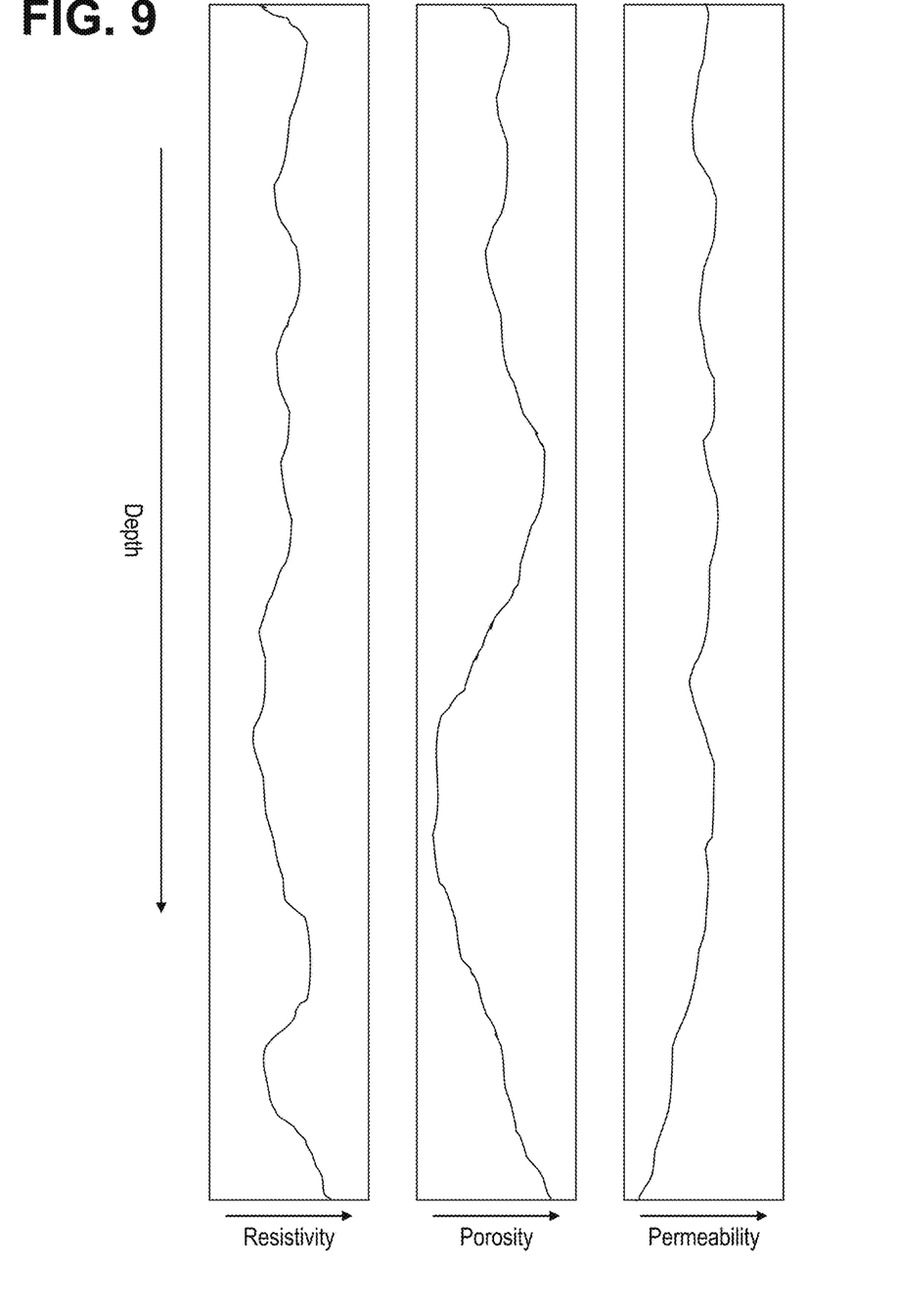
FIG. 9 shows an example of several illustrative well logs of properties of the wellbore.

The methods and systems described herein provide corrected porosity values that allow an improved estimation of hydrocarbons in place within a formation, as well as the estimation of overall field reserves, as compared to existing methods and system. The described corrected porosity values allow reservoir operators to optimize field development and development, while reducing the overall financial risk. The described corrected porosity values also provide a basis for describing models that may be used to determine other formation properties (e.g., resistivity as shown in FIG. 9) and static and/or dynamic simulations (e.g., fluid pressure simulations and/or dynamic fluid flow simulations).

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A method for generating formation properties of a pressurized downhole environment, the method comprising:
    creating a disconnected pore structure by reducing the sizes of pores within a scanned image of a rock sample;
    identifying expanded pores within the rock sample that have expanded due to pressure differential between the pressurized downhole environment and a surface, and generating an expanded pore image based on said expanded pores;
    combining the expanded pore image with the scanned image to create an expansion mask;
    generating a grain conditioning volume based on at least one unexpanded region of the rock sample and combining the grain conditioning volume with the expansion mask to generate a fill volume image;
    combining the fill volume image with the scanned image to create an unexpanded volume image; and
    generating and presenting to a user the formation properties of the pressurized downhole environment using a model generated based upon the unexpanded volume image.

2. The method of claim 1, wherein generating the grain conditioning volume comprises:
    defining the grain conditioning volume to be of a shape and size equal to the rock sample's volume;
    defining the at least one unexpanded region as a subvolume within the rock sample's volume comprising the least number of expanded pores; and
    mirroring the subvolume in all directions to fill the grain conditioning volume.

3. The method of claim 1, wherein identifying the expanded pores comprises:
    dilating the pores of the disconnected pore structure, measuring the dilated pores and sorting the dilated pores by size;
    setting a threshold size below the largest sorted pore size; and
    identifying one or more of the dilated pores that exceed the threshold size as the expanded pores.

4. The method of claim 3, wherein the dilating is performed at least in part using erosion.

5. The method of claim 3, comprising further expanding the one or more of the dilated pores prior to the creating of the expansion mask.

6. The method of claim 5, further comprising expanding the one or more of the dilated pores by one pixel.

7. The method of claim 1, wherein identifying the expanded pores comprises:
    creating an open map for each voxel of the scanned image;
    determining pore sizes for pore spaces identified by the open map;
    setting a threshold size below the largest pore size within the open map; and
    identifying one or more pores that exceed the threshold size as the expanded pores.

8. The method of claim 7, wherein the determining of pores sizes is based on a hydraulic pore size distribution or on a digital NMR size distribution.

9. The method of claim 7, further comprising:
    computing and comparing a subvolume permeability and a grain conditioning volume permeability;
    if a difference between the subvolume permeability and the grain conditioning volume permeability is less than or equal to a tolerance value, generating and presenting the formation properties to the user; and
    if a difference between the subvolume permeability and the grain conditioning volume permeability is greater than a tolerance value, reducing the threshold size and repeating:
        identifying the expanded pores;
        generating the expanded pore image;
        creating the expanded volume image;
        generating the grain conditioning volume;
        generating the fill volume image;
        creating the unexpanded volume image; and
        computing and comparing the subvolume and grain conditioning volume permeabilities.

10. The method of claim 1, further comprising generating the scanned image using a technique selected from the group consisting of scanning acoustic microscopy (SAM), magnetic resonance imaging (MRI), transmitted laser scanning confocal microscopy (LSCM) and focused ion beam scanning electron microscopy (FIB-SEM).

11. The method of claim 1, wherein reducing the size of the pores within the scanned image comprises applying an erosion technique to said scanned image pores.

12. The method of claim 1, wherein generating the grain conditioning volume comprises:
    defining a shifted version of the scanned image as the grain conditioning volume;
    dividing the scanned image into subvolumes, rearranging said subvolumes within the scanned image, and defining the rearranged scanned image as the grain conditioning volume; or
    omitting regions with large grains within the rock from processing used to generate the grain conditioning volume.

13. The method of claim 1, further comprising determining additional properties of the formation based upon the model or further performing static or dynamic simulations of the formation based upon the model.

14. A system for generating formation properties of a pressurized downhole environment, comprising:
   a memory having expanded porosity conditioning software; and
   one or more processors coupled to the memory, the software causing the one or more processors to:
      create a disconnected pore structure by reducing the sizes of pores within a scanned image of a rock sample;
      identify expanded pores within the rock sample that have expanded due to pressure differential between the pressurized downhole environment and a surface, and generate an expanded pore image based on said expanded pores;
      combine the expanded pore image with the scanned image to create an expansion mask;
      generate a grain conditioning volume based on at least one unexpanded region of the rock sample and combine the grain conditioning volume with the expansion mask to generate a fill volume image;
      combine the fill volume image with the scanned image to create an unexpanded volume image; and
      generate and present to a user the formation properties of the pressurized downhole environment using a model generated based upon the unexpanded volume image.

15. The system of claim 14, wherein the software causes the one or more processors to generating the grain conditioning volume by further causing the one or more processors to:
   define the grain conditioning volume to be of a shape and size equal to the rock sample's volume;
   define the an unexpanded region as a subvolume within the rock sample's volume comprising the least number of expanded pores; and
   mirror the subvolume in all directions to fill the grain conditioning volume.

16. The system of claim 14, wherein the software further causes the one or more processors to identify the expanded pores by further causing the one or more processors to:
   dilate the pores of the disconnected pore structure, measure the dilated pores and sort the dilated pores by size;
   set a threshold size below the largest sorted pore size; and
   identify one or more of the dilated pores that exceed the threshold size as the expanded pores.

17. The system of claim 16, wherein the software causes the one or more processors to dilate the pores at least in part using erosion.

18. The system of claim 16, wherein the software further causes the one or more processors to expand the one or more of the dilated pores prior to creating the expansion mask.

19. The system of claim 18, wherein the software further causes the one or more processors to expand the one or more of the dilated pores by one pixel.

20. The system of claim 14, wherein the software further causes the one or more processors to identify one or more of the dilated pores by further causing the one or more processors to:
   create an open map for each voxel of the scanned image;
   determine pore sizes for pore spaces identified by the open map;
   set a threshold size below the largest pore size within the open map; and
   identify one or more pores that exceed the threshold size as the expanded pores.

21. The system of claim 20, wherein the determination of pores sizes is based on a hydraulic pore size distribution or on a digital NMR size distribution.

22. The system of claim 20, wherein the software further causes the one or more processors to:
   compute and compare a subvolume permeability and a grain conditioning volume permeability;
   if the magnitude of the difference between the subvolume permeability and the grain conditioning volume permeability is less than or equal to a tolerance value, generate and present the formation properties to the user; and
   if the magnitude of the difference between the subvolume permeability and the grain conditioning volume permeability is greater than a tolerance value, reduce the threshold size and repeat causing the one or more processors to:
      identify the expanded pores;
      generate the expanded pore image;
      create the expanded volume image;
      generate the grain conditioning volume;
      generate the fill volume image;
      create the unexpanded volume image; and
      compute and compare the subvolume and grain conditioning volume permeabilities.

23. The system of claim 14, wherein the software further causes the one or more processors to generate the scanned image using a technique selected from the group consisting of scanning acoustic microscopy (SAM), magnetic resonance imaging (MRI), transmitted laser scanning confocal microscopy (LSCM) and focused ion beam scanning electron microscopy (FIB-SEM).

24. The system of claim 14, wherein the software further causes the one or more processors to reduce the size of the pores within the scanned image by causing the one or more processors to apply an erosion technique to said scanned image pores.

25. The system of claim 14, wherein the software further causes the one or more processors to generate the grain conditioning volume by causing the one or more processors to:
   define a shifted version of the scanned image as the grain conditioning volume;
   divide the scanned image into subvolumes, rearrange said subvolumes within the scanned image, and define the rearranged scanned image as the grain conditioning volume; or
   omit regions with large grains within the rock from processing used to generate the grain conditioning volume.

26. The system of claim 14, wherein the model is further used to determine additional properties of the formation or further used as a basis for static or dynamic simulations of the formation.

* * * * *